(12) United States Patent
Antonelli et al.

(10) Patent No.: US 11,918,792 B2
(45) Date of Patent: *Mar. 5, 2024

(54) DOSE DETECTION MODULE FOR A MEDICATION DELIVERY DEVICE

(71) Applicant: Eli Lilly and Company, Indianapolis, IN (US)

(72) Inventors: Matthew Thomas Antonelli, Oakland, CA (US); William Churchill Taliaferro Burke, San Francisco, CA (US); Roy Howard Byerly, Indianapolis, IN (US); Christopher Robert McCaslin, Alameda, CA (US); Ethan Edward Pease, Sausalito, CA (US); Kenneth Alan Ritsher, Lowell, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/065,159

(22) Filed: Dec. 13, 2022

(65) Prior Publication Data
US 2023/0110794 A1 Apr. 13, 2023

Related U.S. Application Data

(63) Continuation of application No. 16/632,450, filed as application No. PCT/US2018/019108 on Feb. 22, 2018, now Pat. No. 11,529,470.
(Continued)

(51) Int. Cl.
*A61M 5/315* (2006.01)

(52) U.S. Cl.
CPC ...... *A61M 5/31568* (2013.01); *A61M 5/3155* (2013.01); *A61M 5/31585* (2013.01);
(Continued)

(58) Field of Classification Search
CPC .. A61M 5/31568; A61M 5/24; A61M 5/3155; A61M 5/31551; A61M 5/31585;
(Continued)

(56) References Cited

U.S. PATENT DOCUMENTS

| 5,509,905 A | 4/1996 | Michel |
| 5,536,240 A | 7/1996 | Edwards et al. |

(Continued)

FOREIGN PATENT DOCUMENTS

| CN | 104519930 A | 4/2015 |
| EP | 2060284 | 5/2009 |

(Continued)

OTHER PUBLICATIONS

Patent Cooperation Treaty International Search Report pertaining to International Application No. PCT/US2018/019108; International Filing Date: Feb. 22, 2018; dated May 9, 2018.
(Continued)

*Primary Examiner* — Dung T Ulsh
(74) *Attorney, Agent, or Firm* — M. Daniel Spillman

(57) ABSTRACT

The present disclosure relates to a dose detection system for use with a medication delivery device in which a dose setting member rotates relative to an actuator during dose delivery. The dose detection system includes a module which is removably attached to the medication delivery device. The module includes a rotation sensor attached to the actuator during dose delivery. A sensed element is attached to the dose setting member and includes surface features detectable by the rotation sensor. The rotation sensor comprises a following member including a contact portion resting against and spring-biased in the direction of the surface features. The contact surface is positioned to move over the surface features during rotation of the sensed element, and the rotation sensor is responsive to the movement of the contact portion over the surface features to detect the rotation of the dose setting member.

19 Claims, 8 Drawing Sheets

Related U.S. Application Data

(60) Provisional application No. 62/547,962, filed on Aug. 21, 2017.

(52) U.S. Cl.
CPC ............. *A61M 2205/332* (2013.01); *A61M 2205/3327* (2013.01); *A61M 2205/3365* (2013.01)

(58) Field of Classification Search
CPC .... A61M 2205/332; A61M 2205/3327; A61M 2205/3365; A61M 2205/3584
See application file for complete search history.

(56) References Cited

U.S. PATENT DOCUMENTS

| | | |
|---|---|---|
| 5,728,074 A | 3/1998 | Castellano et al. |
| 6,277,099 B1 | 8/2001 | Strowe et al. |
| 6,585,698 B1 | 7/2003 | Packman et al. |
| 6,743,202 B2 | 6/2004 | Hirschman et al. |
| 7,008,399 B2 | 3/2006 | Larsen et al. |
| 7,195,616 B2 | 3/2007 | Diller et al. |
| 7,291,132 B2 | 11/2007 | DeRuntz et al. |
| 7,749,786 B2 | 7/2010 | Wells |
| 8,221,356 B2 | 7/2012 | Enggaard et al. |
| 8,257,319 B2 | 9/2012 | Plumptre |
| 8,556,865 B2 | 10/2013 | Krulevitch et al. |
| 8,579,867 B2 | 11/2013 | Harms et al. |
| 8,608,079 B2 | 12/2013 | Larsen |
| 9,078,973 B2 | 7/2015 | Harms et al. |
| 9,186,465 B2 | 11/2015 | Jorgensen et al. |
| 9,345,838 B2 | 5/2016 | Plumptre |
| 9,616,178 B2 | 4/2017 | Butler et al. |
| 9,636,464 B1 | 5/2017 | Binier |
| 9,649,448 B2 | 5/2017 | Madsen |
| 9,675,761 B2 | 6/2017 | Hoeholt et al. |
| 9,750,886 B2 | 9/2017 | Plambech et al. |
| 9,764,095 B2 | 9/2017 | Draper |
| 9,833,576 B2 | 12/2017 | Windum et al. |
| 10,383,996 B2 | 8/2019 | Miller et al. |
| 10,420,895 B2 | 9/2019 | Erbstein et al. |
| 2002/0120655 A1 | 8/2002 | Liu et al. |
| 2004/0210199 A1 | 10/2004 | Atterbury et al. |
| 2006/0153693 A1 | 7/2006 | Flechter et al. |
| 2008/0033369 A1 | 2/2008 | Kohlbrenner et al. |
| 2009/0069742 A1 | 3/2009 | Larsen |
| 2012/0226139 A1 | 9/2012 | Peyman |
| 2014/0194829 A1 | 7/2014 | Baek et al. |
| 2014/0276583 A1 | 9/2014 | Chen et al. |
| 2015/0032059 A1 | 1/2015 | Allerdings et al. |
| 2015/0290396 A1 | 10/2015 | Nagar et al. |
| 2016/0008552 A1 | 1/2016 | Madsen et al. |
| 2016/0030680 A1 | 2/2016 | Veasey et al. |
| 2016/0030683 A1 | 2/2016 | Taylor et al. |
| 2016/0082192 A1 | 3/2016 | Veasey et al. |
| 2016/0082195 A1 | 3/2016 | Atterbury et al. |
| 2016/0213853 A1 | 7/2016 | Despa et al. |
| 2016/0287804 A1* | 10/2016 | Madsen ............... G01D 5/1655 |
| 2016/0287807 A1 | 10/2016 | Madsen et al. |
| 2016/0331906 A1* | 11/2016 | Harms ............. A61M 5/31593 |
| 2016/0378951 A1 | 12/2016 | Gofman et al. |
| 2017/0368263 A1 | 12/2017 | Ploch |
| 2018/0126088 A1 | 5/2018 | Radmer et al. |
| 2018/0147363 A1 | 5/2018 | Hansen et al. |
| 2018/0353700 A1 | 12/2018 | Säll et al. |
| 2018/0369488 A1 | 12/2018 | Carlsson et al. |
| 2019/0022328 A1 | 1/2019 | Schleicher et al. |
| 2019/0022330 A1 | 1/2019 | Schleicher et al. |
| 2019/0083708 A1 | 3/2019 | Säll |
| 2019/0143048 A1 | 5/2019 | Haupt |

FOREIGN PATENT DOCUMENTS

| | | |
|---|---|---|
| EP | 3103492 | 12/2016 |
| EP | 3162398 | 5/2017 |
| EP | 3184137 | 6/2017 |
| JP | H5184672 A | 7/1993 |
| WO | 1990009202 | 8/1990 |
| WO | 1992017231 | 10/1992 |
| WO | 1996019872 | 6/1996 |
| WO | 2003005891 | 1/2003 |
| WO | 2006045525 | 5/2006 |
| WO | 2009062675 | 5/2009 |
| WO | 2013004844 | 1/2013 |
| WO | 2013098421 | 7/2013 |
| WO | 2016180873 | 11/2016 |
| WO | 2016193229 | 12/2016 |
| WO | 2017013464 | 1/2017 |
| WO | 2017092960 | 6/2017 |
| WO | 2017097507 | 6/2017 |
| WO | 2017114768 | 7/2017 |
| WO | 2017148855 | 9/2017 |
| WO | 2018013419 | 1/2018 |
| WO | 2018099795 | 6/2018 |
| WO | 2018104289 | 6/2018 |
| WO | 2018125887 | 7/2018 |
| WO | 2018138016 | 8/2018 |
| WO | 2018160425 | 9/2018 |
| WO | 2019040118 | 2/2019 |

OTHER PUBLICATIONS

Patent Cooperation Treaty Written Opinion of the International Searching Authority pertaining to International Application No. PCT/US2018/019108; International Filing Date: Feb. 22, 2018; dated May 9, 2018.

\* cited by examiner

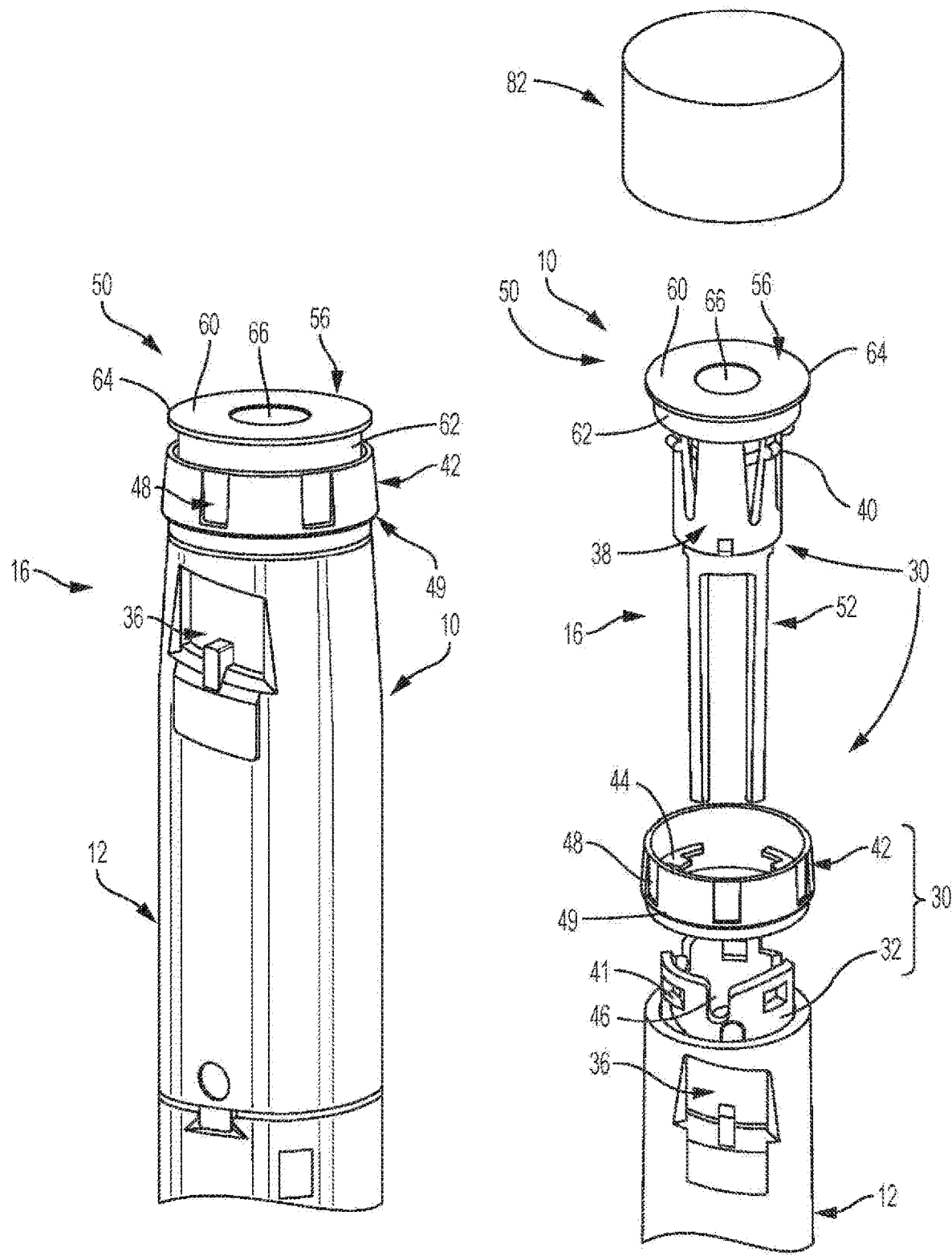

DOSE DETECTION MODULE FOR A MEDICATION DELIVERY DEVICE

TECHNICAL FIELD

The present disclosure relates to an electronic dose detection system for a medication delivery device, and illustratively to an electronic dose detection module adapted to removably attach to a proximal end portion of a medication delivery device. The dose detection system is operable to detect the amount of a dose, of medication delivered by the medication delivery device.

BACKGROUND

Patients suffering from various diseases must frequently inject themselves with medication. To allow a person to conveniently and accurately self-administer medicine, a variety of devices broadly known as pen injectors or injection pens have been developed. Generally, these pens are equipped with a cartridge including a piston and containing a multi-dose quantity of liquid medication. A drive member is movable forward to advance the piston in the cartridge to dispense the contained medication from an outlet at the distal cartridge end, typically through a needle. In disposable or prefilled pens, after a pen has been utilized to exhaust the supply of medication within the cartridge, a user discards the entire pen and begins using a new replacement pen. In reusable pens, after a pen has been utilized to exhaust the supply of medication within the cartridge, the pen is disassembled to allow replacement of the spent cartridge with a fresh cartridge, and then the pen is reassembled for its subsequent use.

Many pen injectors and other medication delivery devices utilize mechanical systems in which members rotate and/or translate relative to one another in a manner proportional to the dose delivered by operation of the device. Accordingly, the art has endeavored to provide reliable systems that accurately measure the relative movement of members of a medication delivery device in order to assess the dose delivered. Such systems may include a sensor which is secured to a first member of the medication delivery device, and which detects the relative movement of a sensed component secured to a second member of the device.

The administration of a proper amount of medication requires that the dose delivered by the medication delivery device be accurate. Many pen injectors and other medication delivery devices do not include the functionality to automatically detect and record the amount of medication delivered by the device during the injection event. In the absence of an automated system, a patient must manually keep track of the amount and time of each injection. Accordingly, there is a need for a device that is operable to automatically detect the dose delivered by the medication delivery device during an injection event. Further, there is a need for such a dose detection device to be removable and reusable with multiple delivery devices.

SUMMARY

In accordance with an aspect of the present disclosure, a dose detection system is provided for a medication delivery device which includes a dose setting member which rotates relative to an actuator during dose delivery. The dose detection system comprises an electronics assembly attached to the actuator and a sensed element attached to the dose setting member. The electronics assembly includes a rotation sensor operable with the sensed element to detect the movement of the dose setting member relative to the actuator during dose delivery. The electronics assembly may further include various additional components such as one or more other sensors, memory, a processor, a controller, a battery, etc.

In another aspect, the dose detection system comprises a module which is removably attachable to the medication delivery device. Among other advantages, the attachable and detachable module is operative to detect a delivered medication amount without changing the functionality or operation of the medication delivery device to which it is attached. In some embodiments, the sensing system records the size of the delivered dose and communicates the information to an external device. The device may include a cartridge and a medication contained within said cartridge. Other advantages will be recognized by those of ordinary skill in the art.

BRIEF DESCRIPTION OF THE DRAWINGS

The features and advantages of the present disclosure will become more apparent to those skilled in the art upon consideration of the following detailed description taken in conjunction with the accompanying figures.

FIG. 3 is a perspective view of the proximal portion of the exemplary medication delivery device of FIG. 1.

FIG. 4 is a partially-exploded, perspective view of the proximal portion of the exemplary medication delivery device of FIG. 1, and showing a dose detection module.

DETAILED DESCRIPTION

Figure 1:
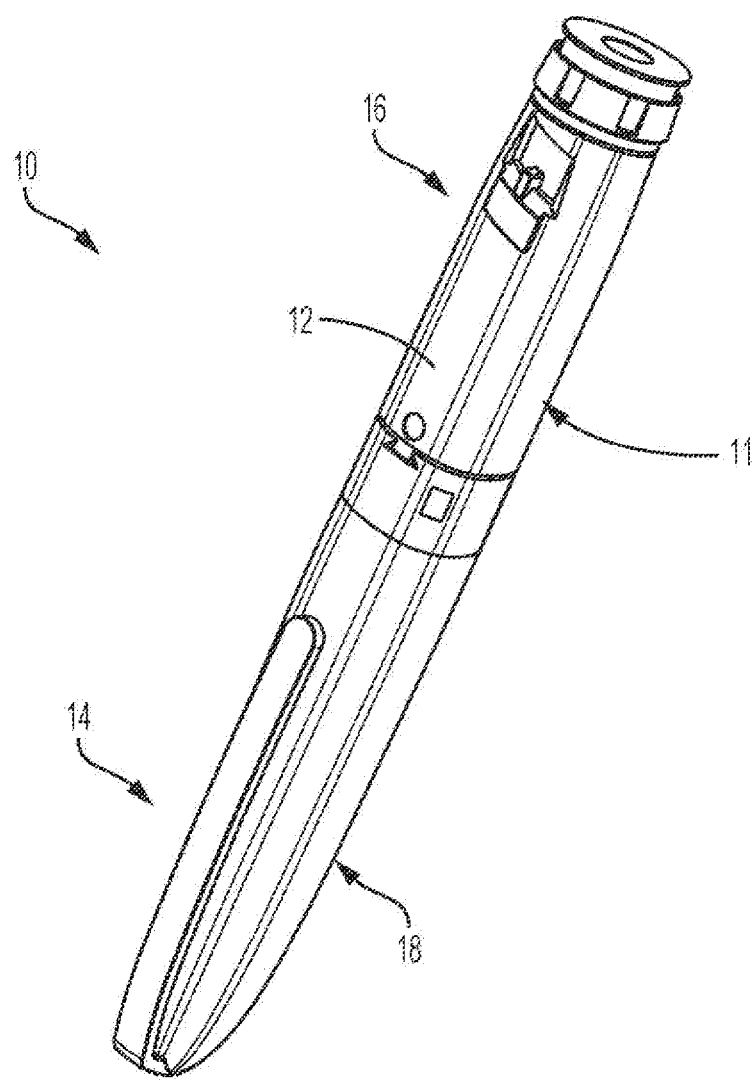
FIG. 1 is a perspective view of an exemplary medication delivery device with which the dose detection system of the present disclosure is operable.

For the purposes of promoting an understanding of the principles of the present disclosure, reference will now be made to the embodiments illustrated in the drawings, and specific language will be used to describe the same. It will nevertheless be understood that no limitation of the scope of the invention is thereby intended.

The present disclosure relates to sensing systems for medication delivery devices. In one aspect, the sensing system is for determining the amount of a dose delivered by a medication delivery device based on the sensing of relative rotational movement between a dose setting member and an actuator of the medication delivery device. The sensed relative rotational movements are correlated to the amount of the dose delivered. By way of illustration, the medication delivery device is described in the form of a pen injector. However, the medication delivery device may be any device which is used to set and to deliver a dose of a medication, such as a pen injector, an infusion pump or a syringe. The medication may be any of a type that may be delivered by such a medication delivery device.

Devices described herein, such as a device 10, may further comprise a medication, such as for example, within a reservoir or cartridge 20. In another embodiment, a system may comprise one or more devices including device 10 and a medication. The term "medication" refers to one or more therapeutic agents including but not limited to insulins, insulin analogs such as insulin lispro or insulin glargine, insulin derivatives, GLP-1 receptor agonists such as dulaglutide or liraglutide, glucagon, glucagon analogs, glucagon derivatives, gastric inhibitory polypeptide (GIP), GIP analogs, GIP derivatives, oxyntomodulin analogs, oxyntomodulin derivatives, therapeutic antibodies and any therapeutic agent that is capable of delivery by the above device. The medication as used in the device may be formulated with one or more excipients. The device is operated in a manner generally as described above by a patient, caregiver or healthcare professional to deliver medication to a person.

Figure 2:
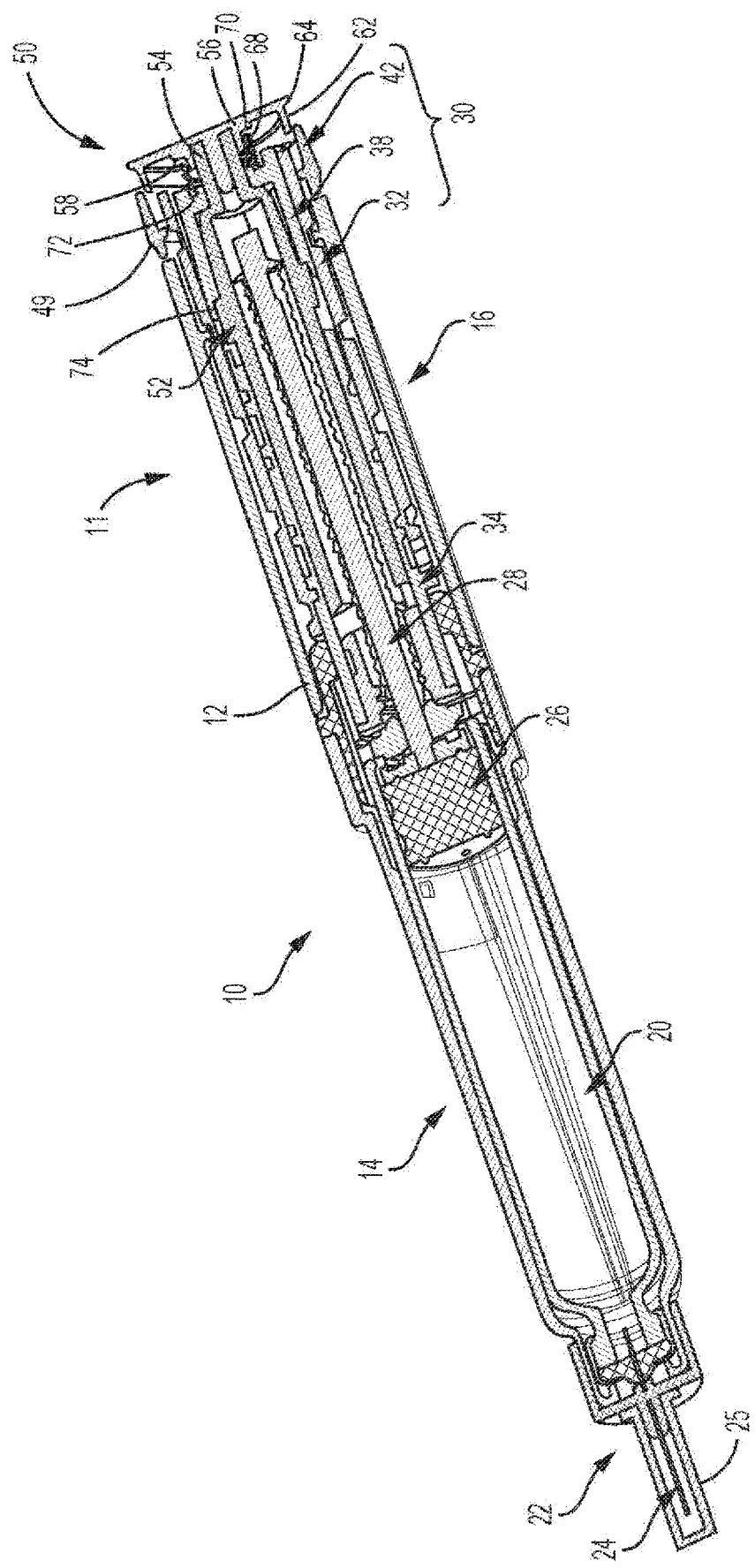
FIG. 2 is a cross-sectional perspective view of the exemplary medication delivery device of FIG. 1.

An exemplary medication delivery device 10 is illustrated in FIGS. 1-4 as a pen injector configured to inject a medication into a patient through a needle. Pen injector 10 includes a body 11 comprising an elongated, pen-shaped housing 12 including a distal portion 14 and a proximal portion 16. Distal portion 14 is received within a pen cap 18. Referring to FIG. 2, distal portion 14 contains a reservoir or cartridge 20 configured to hold the medicinal fluid to be dispensed through its distal outlet end during a dispensing operation. The cartridge 20 of the medication delivery device the medication contained within the cartridge. The outlet end of distal portion 14 is equipped with a removable needle assembly 22 including an injection needle 24 enclosed by a removable cover 25.

A piston 26 is positioned in reservoir 20. An injecting mechanism positioned in proximal portion 16 is operative to advance piston 26 toward the outlet of reservoir 20 during the dose dispensing operation to force the contained medicine through the needled end. The injecting mechanism includes a drive member 28, illustratively in the form of a screw, axially moveable relative to housing 12 to advance piston 26 through reservoir 20.

A dose setting member 30 is coupled to housing 12 for setting a dose amount to be dispensed by device 10. In the illustrated embodiment, dose setting member 30 is in the form of a screw element operative to spiral (i.e., simultaneously move axially and rotationally) relative to housing 12 during dose setting and dose dispensing. FIGS. 1 and 2 illustrate the dose setting member 30 fully screwed into housing 12 at its home or zero dose position. Dose setting member 30 is operative to screw out in a proximal direction from housing 12 until it reaches a fully extended position corresponding to a maximum dose deliverable by device 10 in a single injection.

Referring to FIGS. 2-4, dose setting member 30 includes a cylindrical dose dial member 32 having a helically threaded outer surface that engages a corresponding threaded inner surface of housing 12 to allow dose setting member 30 to spiral relative to housing 12. Dose dial member 32 further includes a helically threaded inner surface that engages a threaded outer surface of sleeve 34 (FIG. 2) of device 10. The outer surface of dial member 32 includes dose indicator markings, such as numbers that are visible through a dosage window 36 to indicate to the user the set dose amount. Dose setting member 30 further includes a tubular flange 38 that is coupled in the open proximal end of dial member 32 and is axially and rotationally locked to dose dial member 32 by detents 40 received within openings 41 in dial member 32. Dose setting member 30 further includes a skirt or collar 42 positioned around the outer periphery of dial member 32 at its proximal end. Skirt 42 is axially and rotationally locked to dial member 32 by tabs 44 received in slots 46 formed by dose dial member 32.

Dose setting member 30 therefore may be considered to comprise any or all of dose dial member 32, flange 38, and skirt 42, as they are all rotationally and axially fixed together. Dose dial member 32 is directly involved in setting the dose and driving delivery of the medication. Flange 38 is attached to dose dial member 32 and, as described later, cooperates with a clutch to selectively couple dose dial member 32 with a dose button.

Skirt 42 provides a surface external of body 11 to enable a user to rotate dose dial member 32 for setting a dose. Skirt 42 illustratively includes a plurality of surface features 48 and an annular ridge 49 formed on the outer surface of skirt 42. Surface features 48 are illustratively longitudinally extending ribs and grooves that are circumferentially spaced around the outer surface of skirt 42 and facilitate a user's grasping and rotating the skirt. In an alternative embodiment, skirt 42 is removed or is integral with dial member 32, and a user may grasp and rotate dose dial member 32 for dose setting.

Delivery device 10 includes an actuator 50 having a clutch 52 which is received within dose dial member 32. Clutch 52 includes an axially extending stem 54 at its proximal end. Actuator 50 further includes dose button 56 positioned proximally of skirt 42 of dose setting member 30. Dose button 56 includes a mounting collar 58 (FIG. 2) centrally located on the distal surface of dose button 56. Collar 58 is attached to stem 54 of clutch 52, such as with an interference fit or an ultrasonic weld, so as to axially and rotatably fix together dose button 56 and clutch 52.

Dose button 56 includes a disk-shaped proximal end surface or face 60 and an annular wall portion 62 extending distally and spaced radially inwardly of the outer peripheral edge of face 60 to form an annular lip 64 therebetween. Face 60 of dose button 56 serves as a push surface against which a force can be applied manually, i.e., directly by the user to push actuator 50 in a distal direction. Dose button 56 illustratively includes a recessed portion 66 centrally located on proximal face 60, although proximal face 60 alternatively may be a flat surface. A bias member 68, illustratively a spring, is disposed between the distal surface 70 of button 56 and a proximal surface 72 of tubular flange 38 to urge actuator 50 and dose setting member 30 axially away from each other. Dose button 56 is depressible by a user to initiate the dose dispensing operation.

Delivery device 10 is operable in both a dose setting mode and a dose dispensing mode. In the dose setting mode of operation, dose setting member 30 is dialed (rotated) relative to housing 12 to set a desired dose to be delivered by device 10. Dialing in the proximal direction serves to increase the set dose, and dialing in the distal direction serves to decrease the set dose. Dose setting member 30 is adjustable in rotational increments (e.g., clicks) corresponding to the minimum incremental increase or decrease of the set dose during the dose setting operation. For example, one increment or "click" may equal one-half or one unit of medication. The set dose amount is visible to the user via the dial indicator markings shown through dosage window 36. Actuator 50, including dose button 56 and clutch 52, move axially and rotationally with dose setting member 30 during the dialing in the dose setting mode.

Dose dial member 32, flange 38 and skirt 42 are all fixed rotationally to one another, and rotate and extend proximally of the medication delivery device 10 during dose setting, due to the threaded connection of dose dial member 32 with housing 12. During this dose setting motion, dose button 56 is rotationally fixed relative to skirt 42 by complementary splines 74 of flange 38 and clutch 52 (FIG. 2), which are urged together by bias member 68. In the course of dose setting, skirt 42 and dose button 56 move relative to housing 12 in a spiral manner from a "start" position to an "end" position. This rotation relative to the housing is in proportion to the amount of dose set by operation of the medication delivery device 10.

Once the desired dose is set, device 10 is manipulated so the injection needle 24 properly penetrates, for example, a user's skin. The dose dispensing mode of operation is initiated in response to an axial distal force applied to the proximal face 60 of dose button 56. The axial force is applied by the user directly to dose button 56. This causes axial movement of actuator 50 in the distal direction relative to housing 12.

The axial shifting motion of actuator 50 compresses biasing member 68 and reduces or closes the gap between dose button 56 and tubular flange 38. This relative axial movement separates the complementary splines 74 on clutch 52 and flange 38, and thereby disengages actuator 50, e.g., dose button 56, from being rotationally fixed to dose setting member 30. In particular, dose setting member 30 is rotationally uncoupled from actuator 50 to allow backdriving rotation of dose setting member 30 relative to actuator 50 and housing 12. Also, since dose setting member 30 and actuator 50 are free to relatively rotate, actuator 50 is held from rotating relative to device housing 12 by the user's engagement of dose button 56 by pressing against it.

As actuator 50 is continued to be axially plunged without rotation relative to housing 12, dial member 32 screws back into housing 12 as it spins relative to dose button 56. The dose markings that indicate the amount still remaining to be injected are visible through window 36. As dose setting member 30 screws down distally, drive member 28 is advanced distally to push piston 26 through reservoir 20 and expel medication through needle 24 (FIG. 2).

During the dose dispensing operation, the amount of medicine expelled from the medication delivery device is proportional to the amount of rotational movement of the dose setting member 30 relative to actuator 50 as the dial member 32 screws back into housing 12. The injection is completed when the internal threading of dial member 32 has reached the distal end of the corresponding outer threading of sleeve 34 (FIG. 2). Device 10 is then once again arranged in a ready state or zero dose position as shown in FIGS. 2 and 3.

The dose delivered may be derived based on the rotation of dose setting member 30 relative to actuator 50 during dose delivery. This rotation may be determined by detecting the incremental movements of the dose setting member which are "counted" as the dose setting member is rotated during dose delivery.

Further details of the design and operation of an exemplary delivery device 10 may be found in U.S. Pat. No. 7,291,132, entitled Medication Dispensing Apparatus with Triple Screw Threads for Mechanical Advantage, the entire disclosure of which is hereby incorporated by reference herein.

The dose detection systems use a sensing component and a sensed component attached to members of the medication delivery device. The term "attached" encompasses any manner of securing the position of a component to another component or to a member of the medication delivery device such that they are operable as described herein. For example, a sensing component may be attached to a member of the medication delivery device by being directly positioned on, received within, integral with, or otherwise connected to, the member. Connections may include, for example, connections formed by frictional engagement, splines, a snap or press fit, sonic welding or adhesive.

The term "directly attached" is used to describe an attachment in which two components, or a component and a member, are physically secured together with no intermediate member, other than attachment components. An attachment component may comprise a fastener, adapter or other part of a fastening system, such as a compressible membrane interposed between the two components to facilitate the attachment. A "direct attachment" is distinguished from an attachment where the components/members are coupled by one or more intermediate functional members, such as the way dose dial member 32 is coupled in FIG. 2 to dose button 56 by clutch 52.

The term "fixed" is used to denote that an indicated movement either can or cannot occur. For example, a first member is "fixed rotationally" with a second member if the two members are required to move together in rotation. In one aspect, a member may be "fixed" relative to another member functionally, rather than structurally. For example, a member may be pressed against another member such that the frictional engagement between the two members fixes them together rotationally, while the two members may not be fixed together absent the pressing of the first member.

Various sensor systems are contemplated herein. In general, the sensor systems comprise a sensing component and a sensed component. The term "sensing component" refers to any component which is able to detect the relative position or movement of the sensed component. The sensing component includes a sensing element, or "sensor", along with associated electrical components to operate the sensing element. The "sensed component" is any component for which the sensing component is able to detect the position and/or movement of the sensed component relative to the sensing component. For the dose detection system, the sensed component rotates relative to the sensing component, which is able to detect the rotational movement of the sensed component. The sensing component may comprise one or more sensing elements, and the sensed component may comprise one or more sensed elements.

The sensor system produces outputs representative of the movement of the sensed component. A controller is operably connected to the sensor to receive the sensor outputs. The controller is configured to determine from the sensor outputs the amount of dose delivered by operation of the medication delivery device.

Illustratively, the dose detection system includes an electronics assembly suitable for operation of the sensor system as described herein. A controller is operably connected to the sensor system to receive outputs from the rotation sensor. The controller is configured to determine from the sensor outputs the amount of dose delivered by operation of the medication delivery device. The controller may include conventional components such as a processor, power supply, memory, microcontrollers, etc. Alternatively, at least some components may be provided separately, such as by means of a computer, smart phone or other device. Means are then provided to operably connect the external controller components with the sensor system at appropriate times, such as by a wired or wireless connection.

An exemplary electronics assembly 76 comprises a flexible printed circuit board (FPCB) having a plurality of electronic components. The electronics assembly comprises a sensor system including one or more sensors operatively communicating with a processor for receiving signals from the sensor representative of the sensed rotation. Electronics assembly 76 further includes a microcontroller unit (MCU) comprising at least one processing core and internal memory. The system includes a battery, illustratively a coin cell battery, for powering the components. The MCU includes control logic operative to perform the operations described herein, including determining a dose delivered by medication delivery device 10 based on a detected rotation of the dose setting member relative to the actuator. Many of the components of the electronics assembly may be contained in a compartment 78 located proximal of the dose button 56.

The MCU is operative to store the detected dose delivery in local memory (e.g., internal flash memory or on-board EEPROM). The MCU is further operative to wirelessly transmit a signal representative of the detected dose to a paired remote electronic device, such as a user's smartphone. Transmission may, for example, be over a Bluetooth low energy (BLE) or other suitable short or long range wireless communication protocol. Illustratively, the BLE control logic and MCU may be integrated on the same circuit.

Further disclosed herein is a medication delivery device including a dose detection system operable to determine the amount of dose delivered based on relative rotation between a dose setting member and the device body. The dose detection system utilizes a dose setting member attached to the device body and rotatable relative to the device body about an axis of rotation during dose delivery. A sensed element is attached to and rotationally fixed with the dose setting member. An actuator is attached to the device body and is held against rotation relative to the device body during dose delivery. The sensed element thereby rotates relative to the actuator during dose delivery in relation to the amount of dose delivered.

The dose detection system involves detecting relative rotational movement between two members. With the extent of rotation having a known relationship to the amount of a delivered dose, the sensor system operates to detect the amount of angular movement from the start of a dose injection to the end of the dose injection. For example, a typical relationship for a pen injector is that an angular displacement of a dose setting member of 18° is the equivalent of one unit of dose, although other angular relationships are also suitable. The sensor system is operable to determine the total angular displacement of a dose setting member dining dose delivery. Thus, if the angular displacement is 90°, then 5 units of dose have been delivered.

The angular displacement is determined by counting increments of dose amounts as the injection proceeds. For example, a sensing system may use a repeating pattern of a sensed element, such that each repetition is an indication of a predetermined degree of angular rotation. Conveniently, the pattern may be established such that each repetition corresponds to the minimum increment of dose that can be set with the medication delivery device.

The sensor system components may be permanently or removably attached to the medication delivery device. In an illustrative embodiment, at least some of the dose detection system components are provided in the form of a module that is removably attached to the medication delivery service. This has the advantage of making these sensor components available for use on more than one pen injector.

The sensor system detects during dose delivery the relative rotation of the sensed component, and therefore of the dose setting member, from which is determined the amount of a dose delivered by the medication delivery device. In an illustrative embodiment, a rotation sensor is attached, and rotationally fixed, to the actuator. The actuator does not rotate relative to the body of the medication delivery device during dose delivery. In this embodiment, a sensed component is attached, and rotationally fixed, to the dose setting member, which rotates relative to the actuator and the device body during dose delivery.

Disclosed herein is a medication delivery device including a dose detection system operable to determine the amount of dose delivered based on relative rotation between a dose setting member and the device body. The dose detection system utilizes a dose setting member attached to the device body and, rotatable relative to the device body about an axis of rotation. A sensed element is attached to and rotationally fixed with the dose setting member. An actuator is attached to the device body and is held against rotation relative to the device body during dose delivery. The sensed element thereby rotates relative to the actuator during dose delivery in relation to the amount of dose delivered.

The sensor system includes a rotation sensor attached to the actuator. The sensed element includes surface features radially-spaced about the axis of rotation of the dose setting member. The rotation sensor includes a following member having a contact portion resting against and spring-biased in the direction of the surface features of the sensed element. The contact surface is thereby positioned to move over the surface features during rotation of the sensed element relative to the actuator during dose delivery. The rotation sensor is responsive to the movement of the contact portion over the surface features and generates signals corresponding to the amount of dose delivery. A controller is responsive to the signals generated by the rotation sensor to determine the amount of dose delivery based on the detected rotation of the dose setting member relative to the actuator during dose delivery.

The surface features may comprise anything detectable by the rotation sensor. As previously indicated, sensor systems may be based on a variety of sensed characteristics, including tactile, optical, electrical and magnetic, for examples. In one aspect, the surface features are physical features which allow for detection of incremental movements as the dose setting member rotates relative to the actuator.

The contact surface is biased against the physical features to ensure proper contact between the contact surface and the physical features during rotation. In one embodiment, the following member is a resilient member having one portion attached to the actuator at a location displaced from the contact surface. For example, the following member may comprise a flexible beam attached at one end to the actuator and having the contact surface at the other end. The beam is flexed to urge the contact surface in the direction of the surface features.

Alternatively, the following member may be biased in any of a variety of other ways. In addition to the use of a resilient beam, the biasing may be provided, for example, by use of a spring component. Such spring component may for example comprise a compression, tension, or torsion coil spring. In yet other embodiments, the following member may be biased against the surface features of the sensed element by a separate resilient member or spring component bearing against the following member.

In one embodiment, the surface features are uniform elements which are spaced intermittently around the axis of rotation of the sensed element. In a particular aspect, the surface features are equi-radially spaced projections separated by intervening recesses. The contact surface of the following member is positioned to ride over the projections, and to move inwardly relative to the intervening recesses. The following member may, for example, be a resilient beam which flexes outwardly along the projections.

In one aspect, the projections are ramped upward in the direction opposite to rotation of the sensed element during dose delivery to facilitate movement of the contact surface along and over the projections. In another aspect, the projections are provided with differing profiles in opposed angular directions to provide for detecting the direction of rotation of the sensed element relative to the actuator. The projections may extend in any direction detectable by the following member. For example, the projections may extend axially or radially. Axial projections may extend proximally or distally. Radial projections may extend inwardly or outwardly.

The sensed element is attached to the dose setting member. Depending on the medication delivery device, the sensed element may be attached to the skirt, the flange or the dose dial, or any other component that rotates relative to the device body during dose delivery in relation to the amount of dose delivered.

In one aspect, the sensing system of dose detection system 80 is originally incorporated into a medication delivery device as an integrated system. In another aspect, there is disclosed a modular form of the dose detection system. The use of a removably attached module is particularly adapted to use with a medication delivery device in which the actuator and/or the dose setting member include portions external to the medication device housing. These external portions allow for direct attachment of the module to the actuator, such as a dose button, and/or attachment of a sensed element to a dose setting member, such as a skirt, flange, or dose dial member, as described herein. Alternately, the sensed element is integral with the medication delivery device and the module is removably attached. This has the advantage that the more complex and expensive electronics, including the rotation sensor and controller, may be reused with different medication delivery devices. By comparison, the sensed element may use relatively simple features, for example radially-spaced projections, which do not add significantly to the cost of the medication delivery device.

Figure 5:
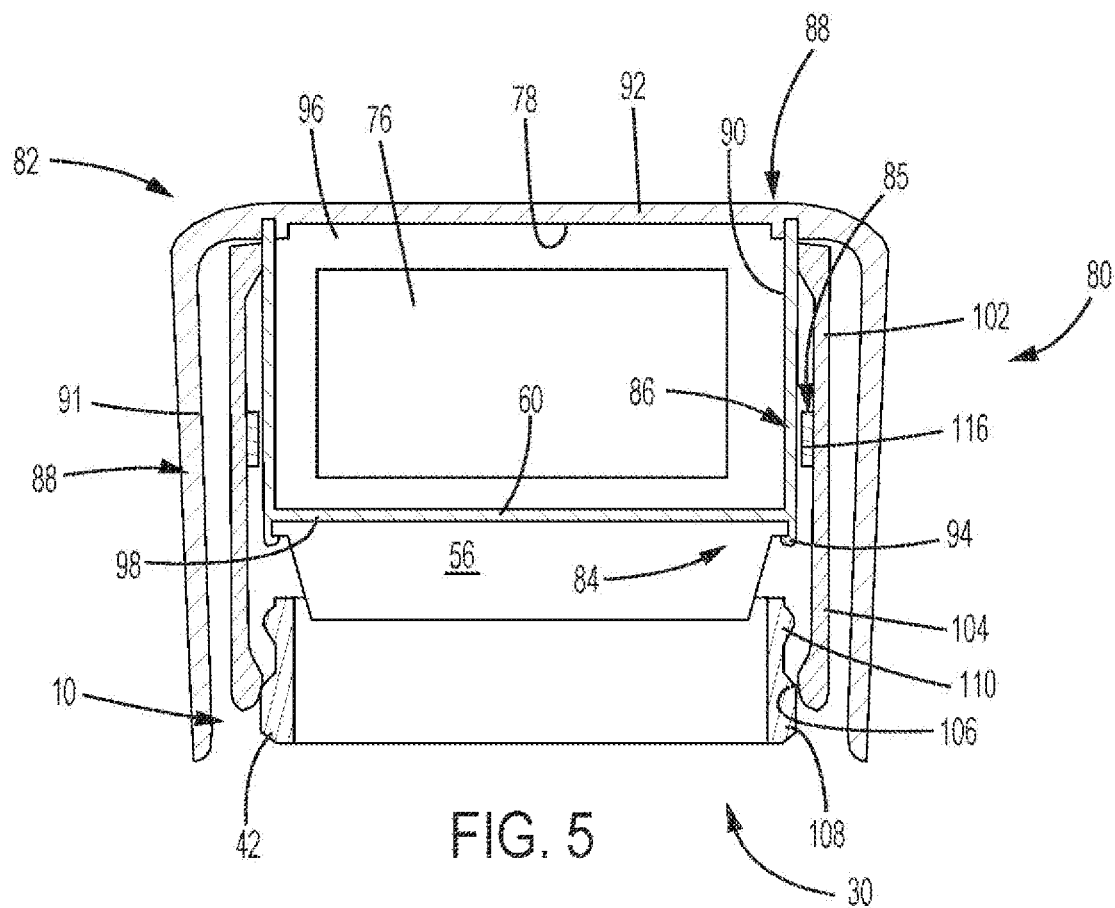
FIG. 5 is a side, diagrammatic view, partially in cross section, of an exemplary embodiment of a dose detection system shown attached to the proximal portion of a medication delivery device.

Referring to FIG. 5, there is shown in diagrammatic form a dose detection system 80 including a module 82 useful in combination with a medication delivery device, such as device 10. Module 82 carries a sensor system, shown generally at 84, including a sensing component 85 comprising a rotation sensor 86 and other associated components such as a processor, memory, battery, etc. Module 82 is provided as a separate component which may be removably attached to the actuator.

Dose detection module 82 includes a body 88 attached to dose button 56. Body 88 illustratively includes an inner wall 90, an outer wall 91, and a top wall 92, spanning over and sealing inner wall 90. By way of example, in FIG. 5 inner wall 90 is diagrammatically shown having inwardly-extending tabs 94 attaching module 82 to dose button 56. Module 82 is thereby attached to dose button 56 such that pressing on the module delivers a set dose.

Dose detection module 82 may alternatively be attached to dose button 56 via any suitable fastening means, such as a snap or press fit, threaded interface, etc., provided that in one aspect module 82 may be removed from a first medication delivery device and thereafter attached to a second medication delivery device. The attachment may be at any location on dose button 56, provided that dose button 56 is able to move any required amount axially relative to dose setting member 30, as discussed herein.

During dose delivery, dose setting member 30 is free to rotate relative to dose button 56 and module 82. In the illustrative embodiment, module 82 is rotationally fixed with dose button 56 and does not rotate during dose delivery. This may be provided structurally, such as with tabs 94 of FIG. 5, or by having mutually-facing splines or other surface features on the module body 88 and dose button 56 engage upon axial movement of module 82 relative to dose button 56. In another embodiment, the distal pressing of the module provides a sufficient frictional engagement between module 82 and dose button 56 as to functionally cause the module 82 and dose button 56 to remain rotationally fixed together during dose delivery.

Top wall 92 is spaced apart from face 60 of dose button 56 and thereby provides with inner wall 90 a compartment 78 containing some or all of electronics assembly 76. Compartment 78 defines a chamber 96 and may be open at the bottom, or may be enclosed, such as by a bottom wall 98. Bottom wall 98 may be positioned to bear directly against face 60 of dose button 56. Alternatively, bottom wall 98, if present, may be spaced apart from dose button 56, and other contacts between module 82 and dose button 56 may be used such that an axial force applied to module 82 is transferred to dose button 56.

Figure 6:
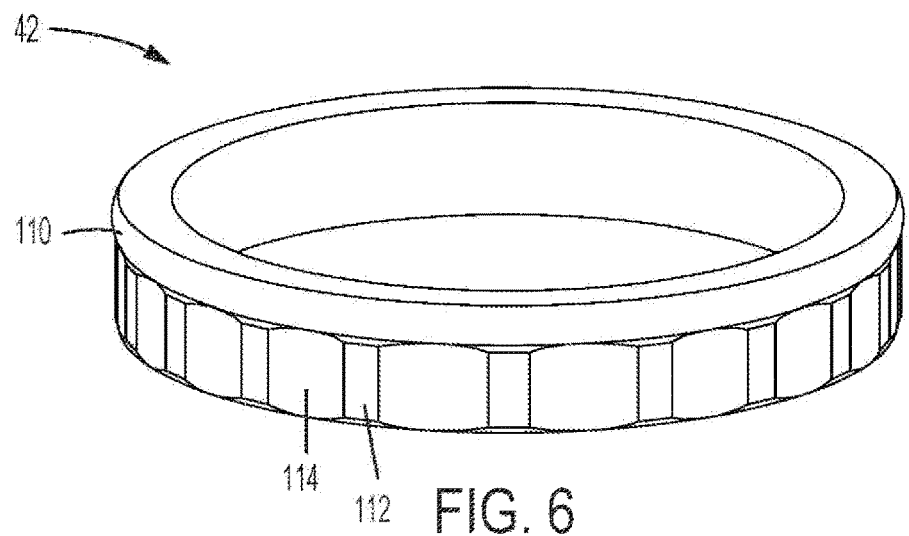
FIG. 6 is a perspective view of an exemplary sensed element useful in the dose detection system.

Referring to FIG. 5, there is diagrammatically shown dose detection system 80 comprising a pair of sensor arms 102 attached at proximal ends to inner wall 90 and configured to operate in connection with sensed element 100. Sensor arms 102 include distal portions 104 having contact surfaces 106. Contact surfaces 106 of sensor arms 102 are positioned in contact with surface features 108 of skirt 42. These surface features 108 detected by contact surfaces 106 may be the same as surface features 48 previously described. Sensor arms 102 are attached to inner wall 90 in a manner which allows contact surfaces 106 to deflect inwardly and outwardly along the surface features 108 as skirt 42 rotates. For example, skirt 42 is shown in FIG. 6 to have a circumferential ridge 110 and a series of equally spaced axial ridges 112 with recessed surfaces 114 therebetween.

The deflection of sensor arms 102 may be accommodated in a variety of ways. For example, the sensor arms may be made of a flexible material which flexes in response to the ridges and recessed surfaces encountered as skirt 42 rotates. Alternatively, sensor arms 102 may be secured to the inner wall with a "living hinge" which spring biases sensor arms 102 in the direction of skirt 42, optionally by including a spring member (not shown).

An accelerometer 116 is mounted to each sensor arm 102, and is electrically connected with the electronics assembly 76. As skirt 42 rotates, contact surfaces 106 successively ride up over each ridge 112 and down into the following recessed surface 114. This deflecting movement results in repeated vibrations that are sensed by the accelerometers and the rotation of skirt 42 is thereby determined.

In the process of being mounted to the medication delivery device, contact surfaces 106 pass over circumferential ridge 110 on skirt 42. This deflection may be separately detected by the accelerometers to signal that module 82 has been pressed axially to or beyond this point. This detection in one embodiment is used to activate the dose detection system.

Figure 7:
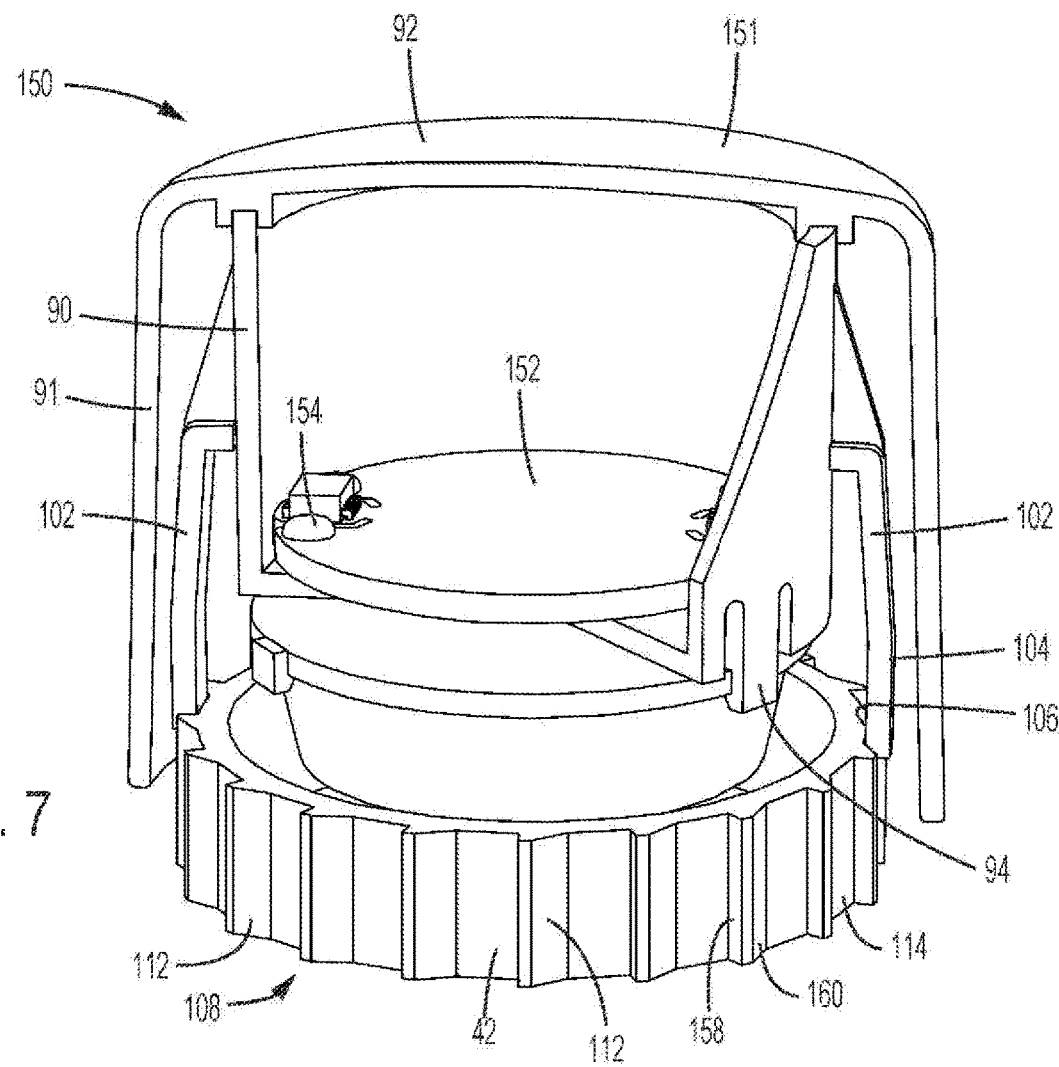
FIG. 7 is a perspective, diagrammatic view, partially in cross section, of a dose detection system according to another exemplary embodiment shown attached to the proximal portion of a medication delivery device.
Figures 8, 9:
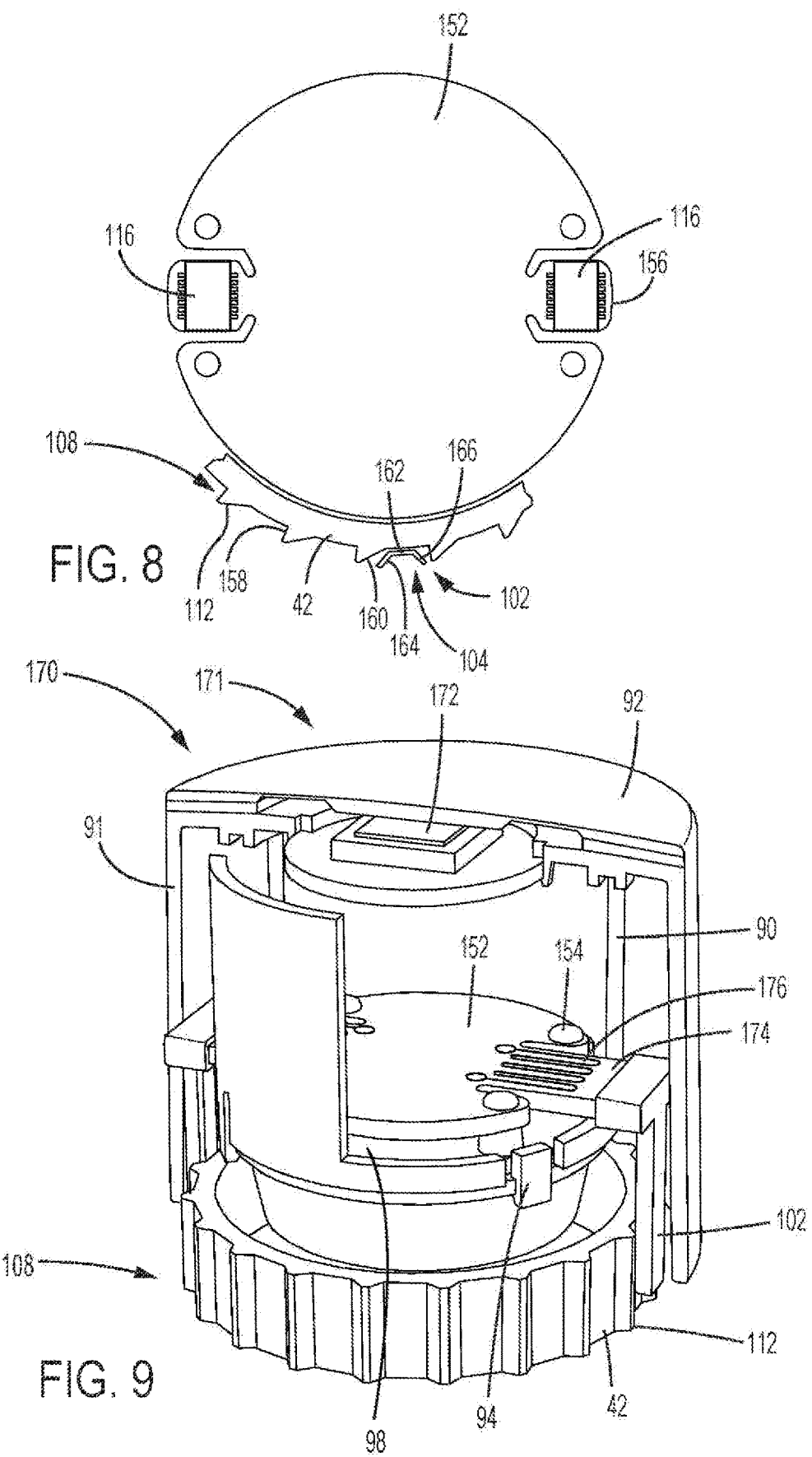
FIG. 8 is a partial plan view of the dose detection system of FIG. 7, and particularly showing the positioning of a sensor arm relative to the outer surface of a dose setting member.
FIG. 9 is a perspective, diagrammatic view, partially in cross section, of a dose detection system according to yet another exemplary embodiment.

In FIGS. 7-8 there is shown an alternate dose detection system 150 including module 151 generally constructed in a manner similar to FIG. 5. Module 151 includes inner wall 90, outer wall 91 and top wall 92. Inner wall 90 is secured in a snap fit to dose button 56 by tabs 94. Cantilevered sensor arms 102 are attached to inner wall 90 and extend to distal portions 104, terminating in contact surfaces 106. Module 151 is shown in FIG. 7 in the at rest position. In this position, contact surfaces 106 rest within upper portions of recessed surfaces 114. When module 151 is pressed distally to initiate a dose, contact surfaces 106 slide distally within the respective recessed surfaces 114 to a lowered position, but still adjacent to surface features 108.

Illustratively, module 151 shown in FIG. 7 includes an outer wall 91 which extends axially distally of inner wall 90. In this manner, outer wall 91 covers the interior components in order to facilitate their operation as described herein. Outer wall 91 may further extend axially distally to fully cover sensor arms 102 and even skirt 42.

Electronics assembly 76 includes a printed circuit board ("PCB") 152 attached to the inner wall by fasteners 154. PCB 152 may be provided with a cutout area 156 radially aligned with a respective sensor arm. An accelerometer 116 may be positioned within the cutout area, which enhances the sensing of vibrations of the sensor arms.

Illustratively shown in FIGS. 7 and 8, the surface features 108 may have non-uniform profiles to allow for additional information to be obtained by the sensor system. For example, skirt 42 is shown with angularly-spaced, axially-extending ridges 112. Each ridge has a profile surface 158 facing in one direction which is sloped significantly different from the slope of the profile surface 160 facing in the opposite angular direction. In this manner, rotation of skirt 42 creates characteristic vibrations which differ depending upon the direction of rotation. The sensor system may thereby be used to identify the characteristic vibration in order to determine the direction of rotation of skirt 42.

Contact surface 106 of sensor arm 102 is provided with a generally U-shaped distal portion 104. Distal portion 104 includes a central portion 162 which is shaped to generally conform with the recessed surfaces 114 of skirt 42. Extending in opposite directions from central portion 162 are side portions 164 and 166. The side portions are configured to accommodate rotation of sensor arm 102 in either direction relative to the surface features 106 of skirt 42.

By way of illustration there is shown in FIG. 9 yet another embodiment of a dose detection system. Dose detection system 170 similarly comprises a module 171 including inner wall 90, outer wall 91, top wall 92 and bottom wall 98. Top wall 92 is shown as a compliant material which flexes upon pressing the module in the distal direction. Microswitch 172 is operatively attached to electronics assembly 76 adjacent the center of top wall 92. Pressing module 171 causes top wall 92 to flex inwardly and to thereby trigger microswitch 172 in order to activate the system electronics.

PCB 152 is attached to bottom wall 98 by fasteners 154. Supports 174 extend outwardly from PCB 152 and carry sensor arms 102. Strain gauges 176 extend over supports 174 and are thereby affected by flexing of the support relative to PCB 152 as sensor arms 102 ride over surface features 108 of skirt 42. The axially-extending ridges 112 are shown in FIG. 9 as having identical profiles in both angular directions. However, based upon different reactions of the strain gauges based on the direction of rotation, the direction of rotation may still be discerned for this embodiment.

Figure 10:
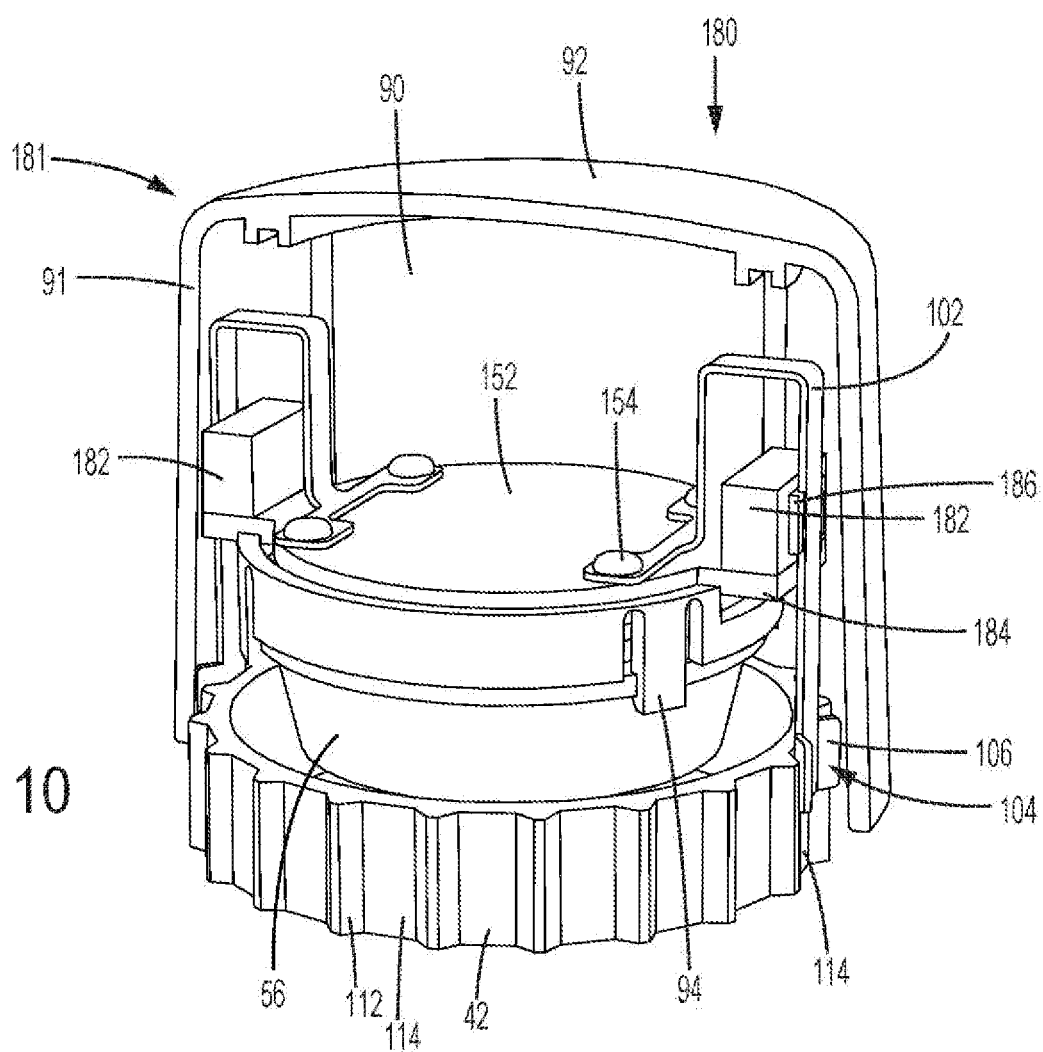
FIG. 10 is a perspective, diagrammatic view, partially in cross section, of another exemplary dose detection system.

FIG. 10 provides another illustration of a dose detection system. System 180 includes module 181, inner wall 90, outer wall 91, and top wall 92. Sensor arms 102 are secured by fasteners 154 to PCB 152. In lieu of the sensors of the previous embodiments, sensor system 180 includes microswitches 182 to detect rotation of skirt 42. Microswitches 182 are attached to mounting extensions 184 of PCB 152 and include buttons 186 positioned to be engaged by sensor arms 102 as they flex inwardly.

Module 181 is shown in FIG. 10 with the contact surfaces 106 received against the recessed surfaces 114 and with microswitch button 186 thereby depressed. As skirt 42 rotates, the distal portions 104 will move in and out relative to button 186 as the contact surfaces 106 successively ride over the ridges 112 and into the recessed surfaces 114. The sensor system operates to detect the rotation of skirt 42 and therefore the amount of dose delivered.

Figure 11:
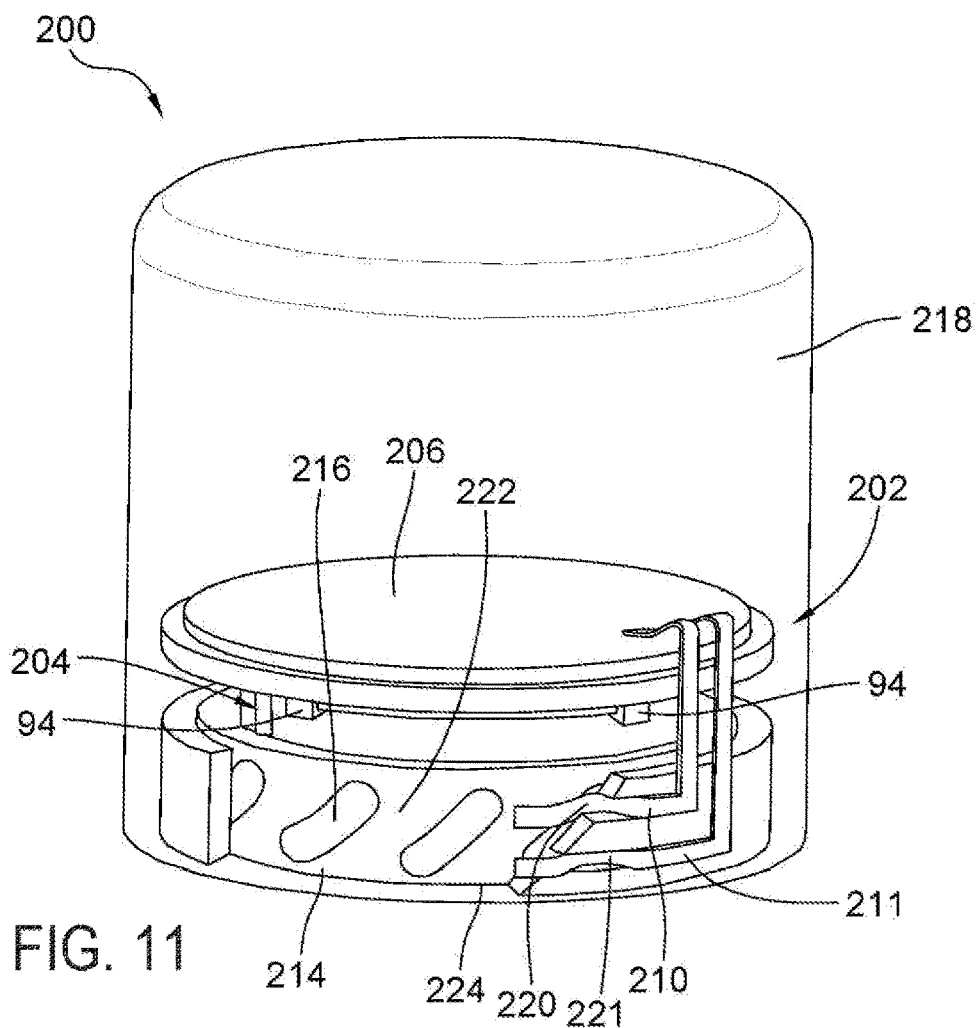
FIG. 11 is a schematic, perspective view of an alternate dose detection system.
Figure 12:
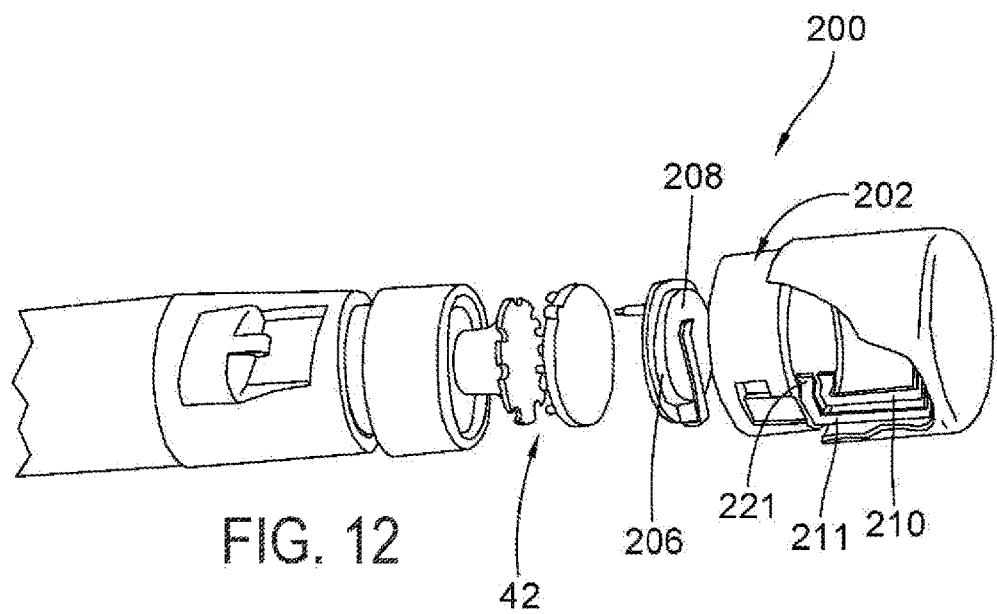
FIG. 12 is an exploded, perspective view of the alternate dose detection system of FIG. 11.

Referring to FIGS. 11-12, there is shown an alternate dose detection system utilizing electrical conductors for detecting rotation of the dose setting element relative to the actuator. Dose detection system 200 includes a sensor system 202 attached to dose button 56, such as by tabs 94. Sensor system 202 includes an electronics assembly 204 including, for example, PCB 206, battery 208, and first and second electrical conductors 210, 211, respectively, operably connected with PCB 206.

Sensed element 212 comprises a cylindrical member 214 attached to the dose setting member, for example skirt 42. Sensed element 212 includes radially spaced conductive portions 216 which operate with conductors 210, 211 to enable sensor system 202 to detect relative rotation of dose setting member. The electrical conductors are spring-biased against sensed element 212 to facilitate electrical communication between the conductors and conductive portions 216.

As shown in FIG. 11, sensor system 202 is contained by a module 218 in a manner as previously described. Module 218 is shown in FIG. 11 in a depressed condition during dose delivery. In this position, electrical conductors 210, 211 are located radially-opposed to conductive portions 216. In one angular, "coupled" position, as shown in FIG. 11, contact portions 220, 221 of electrical contacts 210, 211 both contact the same conductive portion 216 such that direct electrical communication between the two electrical contacts is accomplished. Upon rotation of sensed element 212 relative to dose button 56, a second angular, "uncoupled" position is reached in which only one of the two contact portions 220, 221 is in contact with a conductive portion 216. In this uncoupled condition, direct electrical connection between the two electrical conductors 210, 211 is not provided by a conductive portion. Thus, sensor system 202 is able to detect the successive coupled and uncoupled conditions to detect rotation of the sensed element.

A cylindrical support 222 may be provided to further support electrical contacts 210. Support 222 may facilitate providing a spring bias of the contact portions 220, 221 against sensed element 212, particularly during axial movement of module 218 between dose setting and dose delivery positions. Support 222 may be provided as a separate component attached to module 218, or may be formed integrally with module 218.

Conductive portions 216 may be provided by sensed element 212 in various fashions, such as by co-molding of the conductive portions with a supporting material 224. As a further feature of dose detection system 200, sensed element 212 may be used to identify the type of medication or delivery device. For this purpose, support material 224 is provided with a predetermined conductivity representative of a particular medication or delivery device. When the sensed element is positioned such that electrical conductors are not directly electrically connected by conductive portions 216, there is still provided a sufficient electrical connection of conductors 210, 211 as to be detected by sensor system 202. Thus, support material 224 is selected to provide an electrical property in the uncoupled condition to identify the type of medication or delivery device.

It will further be appreciated that module 218 moves axially in a proximal direction to convert from the dose delivery position shown in FIG. 11 to an idle or dose setting position. Support 222 closely holds first conductor 210 and second conductor 211 during such movement. In addition, movement into the dose setting position will remove first conductor 210 from a position in contact with conductive portions 216. This position may also be used to detect the type of medication and/or delivery device. Movement then to the dose delivery position, and initial coupling of the first and second conductors, may then also be used as an indication that dose delivery has been instituted.

The invention claimed is:

1. A dose detection module for a medication delivery device, the medication delivery device including a device body, a dose setting member attached to said device body and rotatable relative to said device body about an axis of rotation during at least one of dose setting and dose delivery, an actuator attached to said device body, said actuator being axially and rotationally fixed with said dose setting member in a first operating mode during dose setting, the dose detection module comprising:
a module body attachable to the actuator;
a sensed element rotationally fixed with said dose setting member, said sensed element including alternating surface features radially-spaced about the axis of rotation of said dose setting member;
a rotation sensor including a following member, the following member extending axially and including a contact portion resting radially against said sensed element, the contact portion being positioned to move over the surface features during rotation of said sensed element relative to the following member, said rotation sensor being responsive to the movement of the contact portion over the surface features to detect the rotation of the dose setting member; and
a controller responsive to said rotation sensor to determine data based on the detected rotation of said dose setting member.

2. The dose detection module of claim 1 in which the surface features comprise alternating radial projections and recesses.

3. The dose detection module of claim 2 in which said dose setting member comprises an exterior surface exposed outside of said device body, said sensed element being removably attached to the exposed exterior surface.

4. The dose detection module of claim 1 in which in response to movement of the contact portion relative to the surface features rotation vibrations are generated, said rotation sensor being responsive to the rotation vibrations to detect the rotation of the dose setting member.

5. The dose detection module of claim 4 in which said rotation sensor comprises an accelerometer configured to detect the rotation vibrations.

6. The dose detection module of claim 1 in which said rotation sensor comprises a strain gauge detecting the surface features of said sensed element.

7. The dose detection module of claim 1 in which said rotation sensor comprises a microswitch detecting the surface features of said sensed element.

8. The dose detection module of claim 1 in which the projections include a first surface facing in a first angular direction and a second surface facing in a second angular direction opposite to the first angular direction, at least one of the surface features having a ramp-like configuration upon which the contact portion rides up during rotation of said sensed element.

9. The dose detection module of claim 1 in which said module body includes an outer wall defining a compartment, the outer wall extending distally beyond the following member.

10. The dose detection module of claim 9 in which said module body includes an inner wall, the following member attached to and extending distally from the inner wall.

11. The dose detection module of claim 1 in which said surface features are electrical conductor portions, and the rotation sensor and the following member define an electrical contact portion, the module including a printed circuit board within the compartment, the electrical contact portion being attached to and extending distally from the printed circuit board.

12. A medication delivery device, comprising:
a device body;
a dose setting member attached to said device body and rotatable relative to said device body about an axis of rotation during at least one of dose setting and dose delivery;
an actuator attached to said device body, said actuator being rotationally fixed with said dose setting member in a first operating mode during dose setting;
a dose detection module comprising:
a module body attachable to the actuator;
a sensed element attached to and rotationally fixed with said dose setting member, said sensed element including alternating surface features radially-spaced about the axis of rotation of said dose setting member;
a rotation sensor including a following member, the following member extending axially and including a contact portion resting radially against said sensed element, the contact portion being positioned to move over the surface features during rotation of said sensed element relative to the following member, said rotation sensor being responsive to the movement of the contact portion over the surface features to detect the rotation of the dose setting member; and
a controller responsive to said rotation sensor to determine data based on the detected rotation of said dose setting member.

13. The medication delivery device of claim 12 in which the surface features comprise alternating radial projections and recesses.

14. The medication delivery device of claim 12 in which in response to movement of the contact portion relative to the surface features rotation vibrations are generated, said rotation sensor being responsive to the rotation vibrations to detect the rotation of the dose setting member.

15. The medication delivery device of claim 12 in which said rotation sensor comprises a strain gauge detecting the surface features of said sensed element.

16. The medication delivery device of claim 12 in which said rotation sensor comprises a microswitch detecting the surface features of said sensed element.

17. The medication delivery device of claim 12 in which said surface features are electrical conductor portions, and the rotation sensor and the following member define an electrical contact portion, the module including a printed circuit board within the compartment, the electrical contact portion being attached to and extending distally from the printed circuit board.

18. The medication delivery device of claim 12 in which the device body includes a reservoir and a medication contained within said reservoir.

19. A method of dose sensing with a medication delivery device, comprising:
   providing a medication delivery device with a device body, a dose setting member attached to said device body and rotatable relative to said device body about an axis of rotation during at least one of dose setting and dose delivery, an actuator attached to said device body, said actuator being rotationally fixed with said dose setting member in a first operating mode during dose setting, a dose detection module including a module body attachable to the actuator, a sensed element attached to and rotationally fixed with said dose setting member, said sensed element including alternating surface features radially-spaced about the axis of rotation of said dose setting member, a rotation sensor including a following member, the following member extending axially and including a contact portion resting radially against said sensed element, the contact portion being positioned to move over the surface features during rotation of said sensed element relative to the following member, and a controller responsive to said rotation sensor;
   detecting relative movement between the contact portion and the surface features; and
   determining data, with the controller, based on the detected relative movement.

* * * * *